United States Patent
Larsen et al.

(10) Patent No.: US 10,850,041 B2
(45) Date of Patent: Dec. 1, 2020

(54) DRUG DELIVERY DEVICE WITH INFORMATION CAPTURE

(71) Applicant: Novo Nordisk, Bagsvaerd (DK)

(72) Inventors: Andre Larsen, Dragoer (DK); Henrik Riehm Soerensen, Silkeborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 196 days.

(21) Appl. No.: 15/772,619

(22) PCT Filed: Nov. 9, 2016

(86) PCT No.: PCT/EP2016/077070
§ 371 (c)(1),
(2) Date: May 1, 2018

(87) PCT Pub. No.: WO2017/081051
PCT Pub. Date: May 18, 2017

(65) Prior Publication Data
US 2019/0117900 A1 Apr. 25, 2019

(30) Foreign Application Priority Data

Nov. 11, 2015 (EP) ..................................... 15194041
Apr. 1, 2016 (EP) ..................................... 16163474

(51) Int. Cl.
*A61M 5/31* (2006.01)
*A61M 5/315* (2006.01)

(52) U.S. Cl.
CPC ...... *A61M 5/31568* (2013.01); *A61M 5/3157* (2013.01); *A61M 5/31553* (2013.01);
(Continued)

(58) Field of Classification Search
CPC .......... A61M 5/31568; A61M 5/31583; A61M 5/3157; A61M 5/31586; A61M 5/31553; A61M 2005/3125; A61M 2005/3126; A61M 2205/3327; A61M 2205/3584; A61M 2205/52; A61M 2205/581; A61M 2205/6054; A61M 2205/3317; A61M 2205/50; A61M 2205/502
See application file for complete search history.

(56) References Cited

U.S. PATENT DOCUMENTS 3,752,964 A 8/1973 Barnes
5,731,707 A 3/1998 Andermo
(Continued)

FOREIGN PATENT DOCUMENTS

CN 102458533 A 5/2012
CN 103228305 A 7/2013
(Continued)

*Primary Examiner* — Amber S Stiles
(74) *Attorney, Agent, or Firm* — Wesley Nicolas (57) ABSTRACT

A drug delivery device is provided comprising or adapted to receive a cartridge with an axially displaceable piston. The drug delivery device comprises a housing, a stationary capacitive sensor assembly, and a moveable indicator element comprising a surface with a code pattern detectable by the stationary capacitive sensor. The code pattern is formed from conductive markings printed onto the surface. The capacitive sensor is formed on a flexible sheet mounted at least in part to the exterior of the housing.

15 Claims, 8 Drawing Sheets

(52) U.S. Cl.
CPC .... *A61M 5/31583* (2013.01); *A61M 5/31586* (2013.01); *A61M 2005/3125* (2013.01); *A61M 2005/3126* (2013.01); *A61M 2205/3317* (2013.01); *A61M 2205/3327* (2013.01); *A61M 2205/3584* (2013.01); *A61M 2205/50* (2013.01); *A61M 2205/502* (2013.01); *A61M 2205/52* (2013.01); *A61M 2205/581* (2013.01); *A61M 2205/6054* (2013.01)

(56) References Cited

U.S. PATENT DOCUMENTS

| | | |
|---|---|---|
| 7,008,399 B2 | 3/2006 | Larsen et al. |
| 8,803,814 B2 | 8/2014 | Andolina |
| 9,152,829 B2 | 10/2015 | Day et al. |
| 9,233,210 B2 | 1/2016 | Bock et al. |
| 10,278,287 B2 | 4/2019 | Wilson et al. |
| 10,383,996 B2 | 8/2019 | Miller et al. |
| 2006/0118612 A1 | 6/2006 | Christoffersen et al. |
| 2009/0318865 A1 | 12/2009 | Moller et al. |
| 2011/0015576 A1 | 1/2011 | Plumptre et al. |
| 2011/0295215 A1* | 12/2011 | Nielsen ............... A61M 5/178 604/257 |
| 2014/0194826 A1 | 7/2014 | Nielsen et al. |
| 2014/0276583 A1 | 9/2014 | Chen et al. |

FOREIGN PATENT DOCUMENTS

| | | |
|---|---|---|
| CN | 103648555 A | 3/2014 |
| CN | 104302555 A | 1/2015 |
| JP | 2008516711 A | 5/2008 |
| JP | 2011154453 A | 8/2011 |
| WO | 07/122253 A1 | 11/2007 |
| WO | 2010/000084 A1 | 1/2010 |
| WO | 2010/052275 A2 | 5/2010 |
| WO | 2010/098928 A1 | 9/2010 |
| WO | 2013004844 A1 | 1/2013 |
| WO | 2013/098421 A1 | 7/2013 |
| WO | 2013120776 A1 | 8/2013 |
| WO | 2014/111335 A1 | 7/2014 |
| WO | 2014/111336 A1 | 7/2014 |
| WO | 2014/111340 A1 | 7/2014 |
| WO | 2014111339 A1 | 7/2014 |
| WO | 2014111343 A1 | 7/2014 |
| WO | 2014/161952 A1 | 10/2014 |
| WO | 2015/075135 A1 | 5/2015 |
| WO | 2015071354 A1 | 5/2015 |
| WO | 2015138093 A2 | 9/2015 |

* cited by examiner

DRUG DELIVERY DEVICE WITH INFORMATION CAPTURE

CROSS-REFERENCE TO RELATED APPLICATIONS

This application is a 35 U.S.C. § 371 National Stage application of International Application PCT/EP2016/077070 (published as WO 2017/081051), filed Nov. 9, 2016, which claims priority to European Patent Applications 15194041.8, filed Nov. 11, 2015 and 16163474.6, filed Apr. 1, 2016, the contents thereof which are incorporated by reference in their entirety.

The present invention relates to drug delivery devices and systems adapted for capturing drug delivery related data in a cost-effective way.

BACKGROUND OF THE INVENTION

In the disclosure of the present invention reference is mostly made to the treatment of diabetes by delivery of insulin, however, this is only an exemplary use of the present invention.

Drug injection devices have greatly improved the lives of patients who must self-administer drugs and biological agents. Drug injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems.

Correspondingly, a number of injection devices with a dose monitoring/acquisition feature have been provided, see e.g. US 2009/0318865, WO 2010/052275 and U.S. Pat. No. 7,008,399. However, most devices of today are without it.

Further, it would be desirable to detect and store information in respect of the specific drug contained in the cartridge loaded or incorporated in the drug delivery device.

Having regard to the above, it is an object of the present invention to provide a drug delivery device and system as well as components therefore which cost-effectively and reliably allows detection, storage and/or display of data related to use of a drug delivery device.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a drug delivery device is provided, comprising or adapted to receive a cartridge with an axially displaceable piston, the drug delivery device comprising a housing, a stationary capacitive sensor assembly, and a moveable indicator element comprising a surface with a code pattern detectable by the stationary capacitive sensor, the code pattern being formed from conductive markings printed onto the surface. The device further comprises a flexible sheet on which is formed or mounted the stationary capacitive sensor assembly, circuitry for energizing the sensor assembly, and communication means adapted to communicate data related to detected code information, wherein the flexible sheet is mounted at least in part to the exterior of the housing. By this arrangement a coding and a corresponding sensor system for a drug delivery device can be provided in a cost-effective and reliable manner.

In a simple exemplary embodiment the circuitry for energizing the sensor assembly may be in the form of galvanic contacts connected to the stationary capacitive sensor assembly, this allowing an external energy source to energize the sensor assembly, e.g. an array of individual capacitive sensors. Galvanic contacts may also provide the communication means allowing external electronic processor circuitry to utilize the capacitive sensor assembly to determine on the basis of a detected code a rotational position of the moveable indicator element, and calculate an expelled or set dose amount based on determined rotational positions of the moveable indicator element.

In another exemplary embodiment the drug delivery device further comprises electronic processor circuitry formed on or mounted to the flexible sheet and associated with the stationary capacitive sensor assembly, the electronic processor circuitry being configured to determine on the basis of detected code a rotational position of the moveable indicator element, and calculate an expelled or set dose amount based on determined rotational positions of the moveable indicator element. In this way a self-contained system is provided.

The drug delivery device may be provided with visual communication means in the form of a display formed on or mounted to the flexible sheet and adapted to display dose related data, the display being controlled by the electronic processor circuitry. The drug delivery device may further comprise a memory formed on or mounted to the flexible sheet and adapted to store dose related data, the memory being controlled by the electronic processor circuitry. In addition, the drug delivery device may be provided with data communication means formed on or mounted to the flexible sheet and adapted to transmit or transfer dose related data to an auxiliary or external device. The device may further comprise an energy source. One or more or all of the stationary capacitive sensor, display, electronic processor circuitry, and energy source may be in the form of printed electronics. The electronic processor circuitry may comprise logging means adapted to create a log for dose amounts of drug expelled from a cartridge by the drug expelling means.

In a further aspect of the invention a drug delivery device as described above is provided in combination with an auxiliary device, the auxiliary device comprising first communication means adapted to receive dose related data detected by the capacitive sensor assembly.

More specifically, the combination comprises further components in the form of electronic processor circuitry configured to determine on the basis of detected code a rotational position of the moveable indicator element, and calculate an expelled or set dose amount based on determined rotational positions of the moveable indicator element, as well as an energy source for energizing the sensor assembly and the electronic processor circuitry, and a memory adapted to store dose related data, the memory being controlled by the electronic processor circuitry. By this arrangement a drug delivery device system comprising a coded drug delivery device and a corresponding sensor system therefor can be provided in a cost-effective manner as the specific arrangement of the different components can be tailored to optimize functionality and cost-effectiveness for a given implementation.

In such a combination the drug delivery device may comprise the electronic processor circuitry, a memory adapted to store dose related data, and the energy source for energizing the sensor assembly and the electronic processor circuitry. To display data the drug delivery device may be provided with a display adapted to display dose related data and being controlled by the electronic processor circuitry. Alternatively dose data may be transmitted to the auxiliary device for display or storage.

The auxiliary device may be adapted to be releasably attached to the drug delivery device, the first communication means being adapted to transfer dose data by galvanic or wireless transmission. Alternatively the auxiliary device may be adapted to be merely associated with the drug delivery device, e.g. arranged within a given (short) distance, the first communication means being adapted to transfer dose data by wireless transmission. The auxiliary device may further comprise second communication means adapted to transfer or transmit received dose related data to an external device, e.g. a smartphone using wireless communication such as Bluetooth or NFC.

For the above-described drug delivery devices the moveable indicator element may be adapted to rotate relative to the stationary capacitive sensor assembly and corresponding to a general axis, the code pattern being indicative of the rotational position of the moveable indicator element relative to the stationary capacitive sensor assembly. The moveable indicator element may be adapted to rotate helically relative to the stationary capacitive sensor assembly, the code pattern being arranged helically on the surface and being indicative of the rotational and/or axial position of the moveable indicator element relative to the stationary capacitive sensor assembly.

In an exemplary embodiment the drug delivery device comprises a dose setting and dose expelling mechanism comprising a scale member provided with a plurality of user-readable dose size indices, the scale member forming the moveable element, the scale member being rotated from an initial position to a set position when a dose is set and rotated from the set position to the initial position when the set dose is expelled, wherein the housing comprises an opening arranged to show a scale member dose size indicia corresponding to a set dose.

The code pattern may be printed on surface portions of the scale member which passes the housing opening as the scale member rotates during dose setting. The code pattern may be printed with material being non-visible to the human eye. A portion of the user-readable dose size indices may be printed with conductive material to provide the code pattern.

In a further aspect of the invention a drug delivery device is provided, the drug delivery device comprising or being adapted to receive a cartridge with an axially displaceable piston.

The drug delivery device comprises a housing, a stationary capacitive sensor assembly, and a moveable indicator element comprising a surface with a code pattern detectable by the stationary capacitive sensor, wherein the code pattern is formed from conductive markings printed onto the surface. By this arrangement a coding for a drug delivery device can be provided in a cost-effective and reliable manner.

The moveable indicator element may be adapted to rotate relative to the stationary capacitive sensor assembly and corresponding to a general axis, the code pattern being indicative of the rotational position of the moveable indicator element relative to the stationary capacitive sensor assembly. The moveable indicator element may adapted to rotate helically relative to the stationary capacitive sensor assembly, the code pattern being arranged helically on the surface and being indicative of the rotational and/or axial position of the moveable indicator element relative to the stationary capacitive sensor assembly.

In an exemplary embodiment the drug delivery device comprises a dose setting and dose expelling mechanism comprising a scale member provided with a plurality of user-readable dose size indices, the scale member forming the moveable element. The scale member is adapted to be rotated from an initial position to a set position when a dose is set and rotated from the set position to the initial position when the set dose is expelled.

The housing may be provided with an opening arranged to show a scale member dose size indicia corresponding to a set dose. The code pattern may be printed on surface portions of the scale member which passes the housing opening as the scale member rotates during dose setting, with the code pattern being printed with material being essentially non-visible to the human eye.

In an alternative configuration a portion of the user-readable dose size indices are printed with conductive material to provide the code pattern. For such an arrangement the capacitive sensor assembly may comprise a plurality of sensor areas arranged circumferentially relative to the scale member.

In an exemplary embodiment the drug delivery device comprises electronic processor circuitry associated with the stationary capacitive sensor assembly and configured to (i) determine on the basis of a detected code a rotational position of the moveable indicator element, and (ii) calculate an expelled or set dose amount based on determined rotational positions of the moveable indicator element. The drug delivery device may comprise a flexible sheet on which is formed or mounted the stationary capacitive sensor, a display adapted to display dose related data, the electronic processor circuitry, and an energy source. The electronic processor circuitry is adapted to control the display to display a dose amount and a time parameter related to the time the dose amount was expelled, and the flexible sheet is mounted at least in part to the exterior of the housing. One or more or all of the stationary capacitive sensor, display, electronic processor circuitry, and energy source may be in the form of printed electronics. The electronic processor circuitry may comprise logging means adapted to create a log for dose amounts of drug expelled from a cartridge by the drug expelling means.

In addition to the coded indicator element the above-described drug delivery devices may further comprise a capacitive sensor assembly adapted to detect a code pattern formed from conductive markings printed onto the surface of a received or contained cartridge.

Thus, in a further aspect of the invention a drug-filled cartridge with an axially displaceable piston and an exterior surface is provided. The exterior surface of the cartridge is provided with user-readable printed information, and a code pattern printed with material being essentially non-visible to the human eye, the code representing one or more properties of the drug contained in the cartridge. The non-visible code may be printed overlapping, i.e. below or above, with the user-readable information.

The drug-filled cartridge may be provided in combination with a drug delivery device adapted to receive the cartridge, the drug delivery device comprising a stationary capacitive sensor assembly adapted to detect the non-visible code. The drug delivery device may comprise electronic processor circuitry associated with the stationary capacitive sensor assembly and configured to retrieve drug-related information from the non-visible code.

As used herein, the term "drug" is meant to encompass any flowable medicine formulation capable of being passed through a delivery means such as a cannula or hollow needle in a controlled manner, such as a liquid, solution, gel or fine suspension, and containing one or more drug agents. The drug may be a single drug compound or a premixed or co-formulated multiple drug compounds drug agent from a single reservoir. Representative drugs include pharmaceuticals such as peptides (e.g. insulins, insulin containing drugs, GLP-1 containing drugs as well as derivatives thereof), proteins, and hormones, biologically derived or active agents, hormonal and gene based agents, nutritional formulas and other substances in both solid (dispensed) or liquid form. In the description of the exemplary embodiments reference will be made to the use of insulin and GLP-1 containing drugs, this including analogues thereof as well as combinations with one or more other drugs.

BRIEF DESCRIPTION OF THE DRAWINGS

In the following embodiments of the invention will be described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The terms "assembly" and "subassembly" do not imply that the described components necessarily can be assembled to provide a unitary or functional assembly or subassembly during a given assembly procedure but is merely used to describe components grouped together as being functionally more closely related.

Figure 1A:
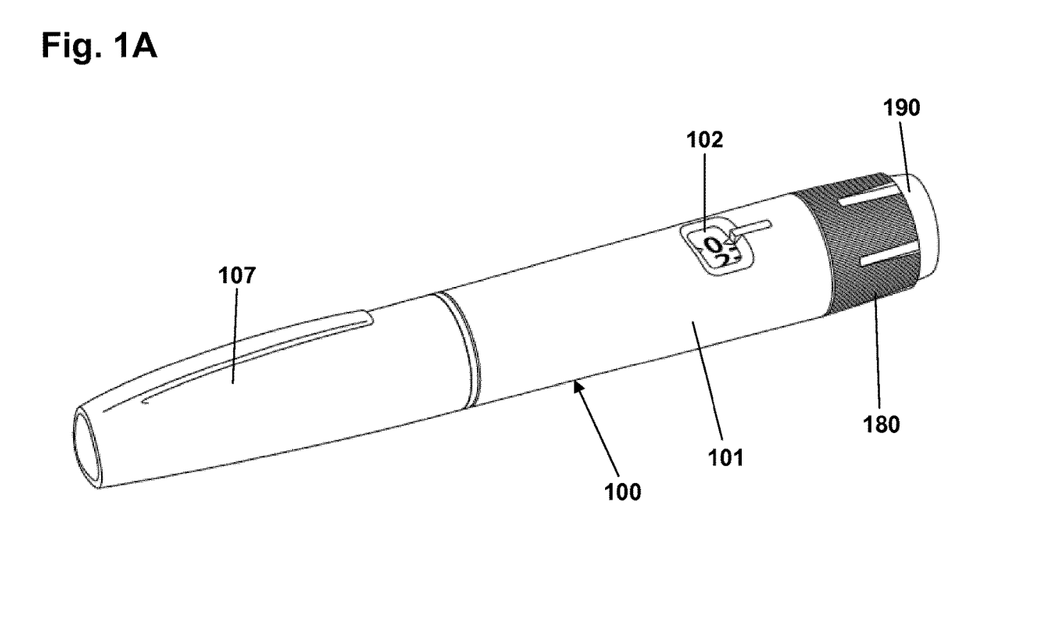
FIG. 1A shows a pen device.
Figure 1B:
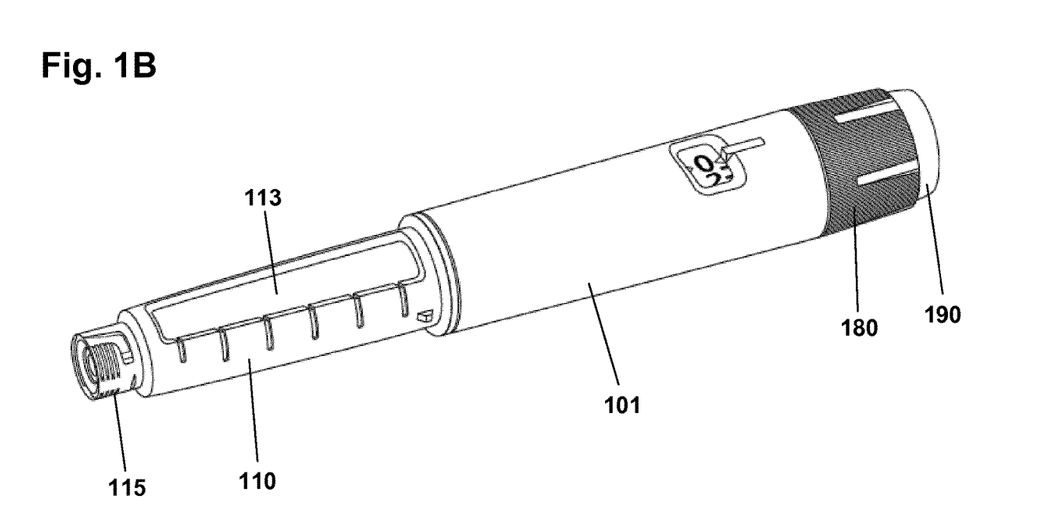
FIG. 1B shows the pen device of FIG. 1A with the pen cap removed.

Before turning to embodiments of the present invention per se, an example of a pre-filled drug delivery will be described, such a device providing the basis for the exemplary embodiments of the present invention. Although the pen-formed drug delivery device 100 shown in FIG. 1 may represent a "generic" drug delivery device, the actually shown device is a FlexTouch® pre-filled drug delivery pen as manufactured and sold by Novo Nordisk A/S, Bagsvaerd, Denmark.

The pen device 100 comprises a cap part 107 and a main part having a proximal body or drive assembly portion with a housing 101 in which a drug expelling mechanism is arranged or integrated, and a distal cartridge holder portion in which a drug-filled transparent cartridge 113 with a distal needle-penetrable septum is arranged and retained in place by a non-removable cartridge holder attached to the proximal portion, the cartridge holder having openings allowing a portion of the cartridge to be inspected as well as distal coupling means 115 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose setting member 180 serves to manually set a desired dose of drug shown in display window 102 and which can then be expelled when the button 190 is actuated. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose, e.g. as in a FlexPen® manufactured and sold by Novo Nordisk A/S.

Although FIG. 1 shows a drug delivery device of the pre-filled type, i.e. it is supplied with a premounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "frontloaded" device in which a cartridge is inserted through a distal opening in the cartridge holder which is non-removable attached to the main part of the device.

As the invention relates to electronic circuitry adapted to be incorporated in and interact with a drug delivery device, an exemplary embodiment of such a device will be described for better understanding of the invention.

Figure 2:
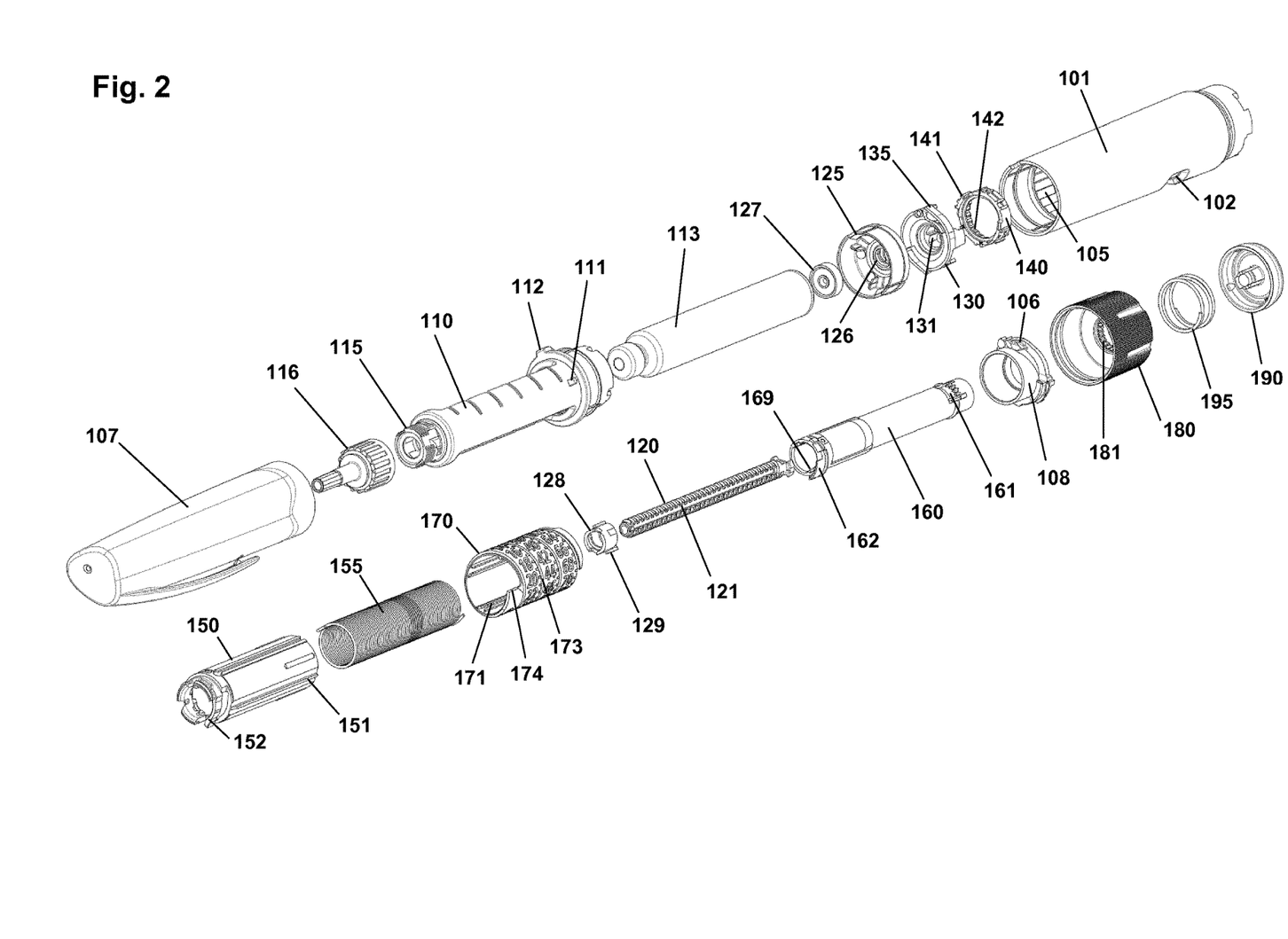
FIG. 2 shows in an exploded view the components of the pen device of FIG. 1A, FIGS. 3A and 3B show in sectional views an expelling mechanism in two states.

FIG. 2 shows an exploded view of the pen-formed drug delivery device 100 shown in FIG. 1. More specifically, the pen comprises a tubular housing 101 with a window opening 102 and onto which a cartridge holder 110 is fixedly mounted, a drug-filled cartridge 113 being arranged in the cartridge holder. The cartridge holder is provided with distal coupling means 115 allowing a needle assembly 116 to be releasable mounted, proximal coupling means in the form of two opposed protrusions 111 allowing a cap 107 to be releasable mounted covering the cartridge holder and a mounted needle assembly, as well as a protrusion 112 preventing the pen from rolling on e.g. a table top. In the housing distal end a nut element 125 is fixedly mounted, the nut element comprising a central threaded bore 126, and in the housing proximal end a spring base member 108 with a central opening is fixedly mounted. A drive system comprises a threaded piston rod 120 having two opposed longitudinal grooves and being received in the nut element threaded bore, a ring-formed piston rod drive element 130 rotationally arranged in the housing, and a ring-formed clutch element 140 which is in rotational engagement with the drive element (see below), the engagement allowing axial movement of the clutch element. The clutch element is provided with outer spline elements 141 adapted to engage corresponding splines 104 (see FIG. 4B) on the housing inner surface, this allowing the clutch element to be moved between a rotationally locked proximal position, in which the splines are in engagement, and a rotationally free distal position in which the splines are out of engagement. As just mentioned, in both positions the clutch element is rotationally locked to the drive element. The drive element comprises a central bore with two opposed protrusions 131 in engagement with the grooves on the piston rod whereby rotation of the drive element results in rotation and thereby distal axial movement of the piston rod due to the threaded engagement between the piston rod and the nut element. The drive element further comprises a pair of opposed circumferentially extending flexible ratchet arms 135 adapted to engage corresponding ratchet teeth 105 arranged on the housing inner surface. The drive element and the clutch element comprise cooperating coupling structures rotationally locking them together but allowing the clutch element to be moved axially, this allowing the clutch element to be moved axially to its distal position in which it is allowed to rotate, thereby transmitting rotational movement from the dial system (see below) to the drive system. The interaction between the clutch element, the drive element and the housing will be shown and described in greater detail with reference to FIGS. 4A and 4B.

On the piston rod an end-of-content (EOC) member 128 is threadedly mounted and on the distal end a washer 127 is rotationally mounted. The EOC member comprises a pair of opposed radial projections 129 for engagement with the reset tube (see below).

Figure 3A:
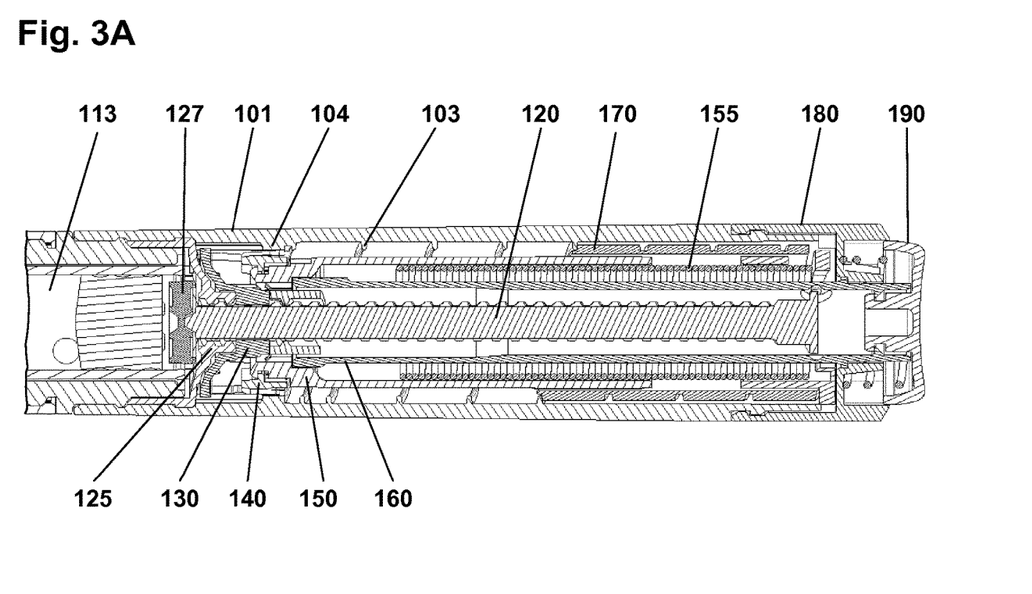

The dial system comprises a ratchet tube 150, a reset tube 160, a scale drum 170 with an outer helically arranged row of dose numerals, a user-operated dial member 180 for setting a dose of drug to be expelled, a release button 190 and a torque spring 155 (see FIG. 3). The reset tube is mounted axially locked inside the ratchet tube but is allowed to rotate a few degrees (see below). The reset tube comprises on its inner surface two opposed longitudinal grooves 169 adapted to engage the radial projections 129 of the EOC member, whereby the EOC can be rotated by the reset tube but is allowed to move axially. The clutch element is mounted axially locked on the outer distal end portion of the ratchet tube 150, this providing that the ratchet tube can be moved axially in and out of rotational engagement with the housing via the clutch element. The dial member 180 is mounted axially locked but rotationally free on the housing proximal end, the dial ring being under normal operation rotationally locked to the reset tube (see below), whereby rotation of dial ring results in a corresponding rotation of the reset tube and thereby the ratchet tube. The release button 190 is axially locked to the reset tube but is free to rotate. A return spring 195 provides a proximally directed force on the button and the thereto mounted reset tube. The scale drum 170 is arranged in the circumferential space between the ratchet tube and the housing, the drum being rotationally locked to the ratchet tube via cooperating longitudinal splines 151, 171 and being in rotational threaded engagement with the inner surface of the housing via cooperating thread structures 103, 173, whereby the row of numerals passes the window opening 102 in the housing when the drum is rotated relative to the housing by the ratchet tube. The torque spring is arranged in the circumferential space between the ratchet tube and the reset tube and is at its proximal end secured to the spring base member 108 and at its distal end to the ratchet tube, whereby the spring is strained when the ratchet tube is rotated relative to the housing by rotation of the dial member. A ratchet mechanism with a flexible ratchet arm 152 is provided between the ratchet tube and the clutch element, the latter being provided with an inner circumferential teeth structures 142, each tooth providing a ratchet stop such that the ratchet tube is held in the position to which it is rotated by a user via the reset tube when a dose is set. In order to allow a set dose to be reduced a ratchet release mechanism 162 is provided on the reset tube and acting on the ratchet tube, this allowing a set dose to be reduced by one or more ratchet increments by turning the dial member in the opposite direction, the release mechanism being actuated when the reset tube is rotated the above-described few degrees relative to the ratchet tube.

Having described the different components of the expelling mechanism and their functional relationship, operation of the mechanism will be described next with reference mainly to FIGS. 3A and 3B.

The pen mechanism can be considered as two interacting systems, a dose system and a dial system, this as described above. During dose setting the dial mechanism rotates and the torsion spring is loaded. The dose mechanism is locked to the housing and cannot move. When the push button is pushed down, the dose mechanism is released from the housing and due to the engagement to the dial system, the torsion spring will now rotate back the dial system to the starting point and rotate the dose system along with it.

The central part of the dose mechanism is the piston rod 120, the actual displacement of the plunger being performed by the piston rod. During dose delivery, the piston rod is rotated by the drive element 130 and due to the threaded interaction with the nut element 125 which is fixed to the housing, the piston rod moves forward in the distal direction. Between the rubber piston and the piston rod, the piston washer 127 is placed which serves as an axial bearing for the rotating piston rod and evens out the pressure on the rubber piston. As the piston rod has a non-circular cross section where the piston rod drive element engages with the piston rod, the drive element is locked rotationally to the piston rod, but free to move along the piston rod axis. Consequently, rotation of the drive element results in a linear forwards movement of the piston. The drive element is provided with small ratchet arms 134 which prevent the drive element from rotating clockwise (seen from the push button end). Due to the engagement with the drive element, the piston rod can thus only move forwards. During dose delivery, the drive element rotates anti-clockwise and the ratchet arms 135 provide the user with small clicks due to the engagement with the ratchet teeth 105, e.g. one click per unit of insulin expelled.

Turning to the dial system, the dose is set and reset by turning the dial member 180. When turning the dial, the reset tube 160, the EOC member 128, the ratchet tube 150 and the scale drum 170 all turn with it. As the ratchet tube is connected to the distal end of the torque spring 155, the spring is loaded. During dose setting, the arm 152 of the ratchet performs a dial click for each unit dialled due to the interaction with the inner teeth structure 142 of the clutch element. In the shown embodiment the clutch element is provided with 24 ratchet stops providing 24 clicks (increments) for a full 360 degrees rotation relative to the housing. The spring is preloaded during assembly which enables the mechanism to deliver both small and large doses within an acceptable speed interval. As the scale drum is rotationally engaged with the ratchet tube, but movable in the axial direction and the scale drum is in threaded engagement with the housing, the scale drum will move in a helical pattern when the dial system is turned, the number corresponding to the set dose being shown in the housing window 102.

The ratchet 152, 142 between the ratchet tube and the clutch element 140 prevents the spring from turning back the parts. During resetting, the reset tube moves the ratchet arm 152, thereby releasing the ratchet click by click, one click corresponding to one unit IU of insulin in the described embodiment. More specifically, when the dial member is turned clockwise, the reset tube simply rotates the ratchet tube allowing the arm of the ratchet to freely interact with the teeth structures 142 in the clutch element. When the dial member is turned counter-clockwise, the reset tube interacts directly with the ratchet click arm forcing the click arm towards the centre of the pen away from the teeth in the clutch, thus allowing the click arm on the ratchet to move "one click" backwards due to torque caused by the loaded spring.

Figure 3B:
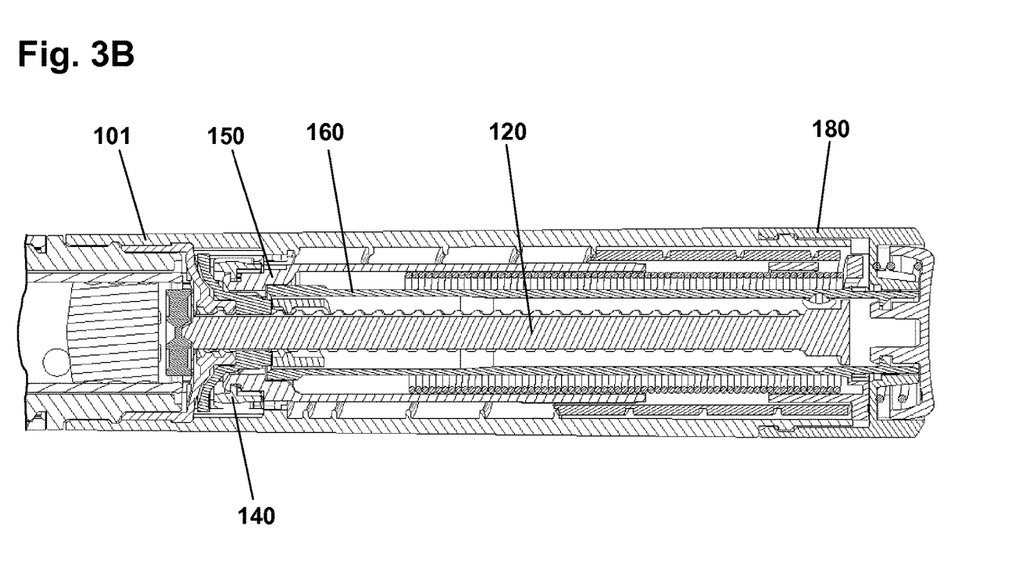

To deliver a set dose, the push button 190 is pushed in the distal direction by the user as shown in FIG. 3B. The reset tube 160 decouples from the dial member and subsequently the clutch element 140 disengages the housing splines 104. Now the dial mechanism returns to "zero" together with the drive element 130, this leading to a dose of drug being expelled. It is possible to stop and start a dose at any time by releasing or pushing the push button at any time during drug delivery. A dose of less than 5 IU normally cannot be paused, since the rubber piston is compressed very quickly leading to a compression of the rubber piston and subsequently delivery of insulin when the piston returns to the original dimensions.

The EOC feature prevents the user from setting a larger dose than left in the cartridge. The EOC member 128 is rotationally locked to the reset tube, which makes the EOC member rotate during dose setting, resetting and dose delivery, during which it can be moved axially back and forth following the thread of the piston rod. When it reaches the proximal end of the piston rod a stop is provided, this preventing all the connected parts, including the dial member, from being rotated further in the dose setting direction, i.e. the now set dose corresponds to the remaining drug content in the cartridge.

The scale drum 170 is provided with a distal stop surface 174 adapted to engage a corresponding stop surface on the housing inner surface, this providing a maximum dose stop for the scale drum preventing all the connected parts, including the dial member, from being rotated further in the dose setting direction. In the shown embodiment the maximum dose is set to 80 IU. Correspondingly, the scale drum is provided with a proximal stop surface adapted to engage a corresponding stop surface on the spring base member, this preventing all the connected parts, including the dial member, from being rotated further in the dose expelling direction, thereby providing a "zero" stop for the entire expelling mechanism.

To prevent accidental over-dosage in case something should fail in the dialling mechanism allowing the scale drum to move beyond its zero-position, the EOC member serves to provide a security system. More specifically, in an initial state with a full cartridge the EOC member is positioned in a distal-most axial position in contact with the drive element. After a given dose has been expelled the EOC member will again be positioned in contact with the drive element. Correspondingly, the EOC member will lock against the drive element in case the mechanism tries to deliver a dose beyond the zero-position. Due to tolerances and flexibility of the different parts of the mechanism the EOC will travel a short distance allowing a small "over dose" of drug to be expelled, e.g. 3-5 IU of insulin.

The expelling mechanism further comprises an end-of-dose (EOD) click feature providing a distinct feedback at the end of an expelled dose informing the user that the full amount of drug has been expelled. More specifically, the EOD function is made by the interaction between the spring base and the scale drum. When the scale drum returns to zero, a small click arm 106 on the spring base is forced backwards by the progressing scale drum. Just before "zero" the arm is released and the arm hits a countersunk surface on the scale drum.

The shown mechanism is further provided with a torque limiter in order to protect the mechanism from overload applied by the user via the dial member. This feature is provided by the interface between the dial member and the reset tube which as described above are rotationally locked to each other. More specifically, the dial member is provided with a circumferential inner teeth structure 181 engaging a number of corresponding teeth arranged on a flexible carrier portion 161 of the reset tube. The reset tube teeth are designed to transmit a torque of a given specified maximum size, e.g. 150-300 Nmm, above which the flexible carrier portion and the teeth will bend inwards and make the dial member turn without rotating the rest of the dial mechanism. Thus, the mechanism inside the pen cannot be stressed at a higher load than the torque limiter transmits through the teeth.

Having described the working principles of a mechanical drug delivery device, exemplary embodiments of the present invention will be described.

As appears from the above description of a drug delivery device with a scale drum which rotates in a first direction during dose setting and in the opposite direction during dose expelling, the rotational positions between the beginning and the end of an out-dosing event would be indicative of the amount of drug expelled and, most likely, injected.

Correspondingly, in accordance with a first aspect of the present invention, an embodiment of a drug delivery device will be described which in a simple and cost-effective way is adapted to detect the size of an expelled dose of drug. More specifically, a drug delivery is provided with a stationary capacitive sensor assembly and a moveable indicator element in the form of a scale drum comprising an outer surface with a code pattern detectable by the stationary capacitive sensor.

Figure 4:
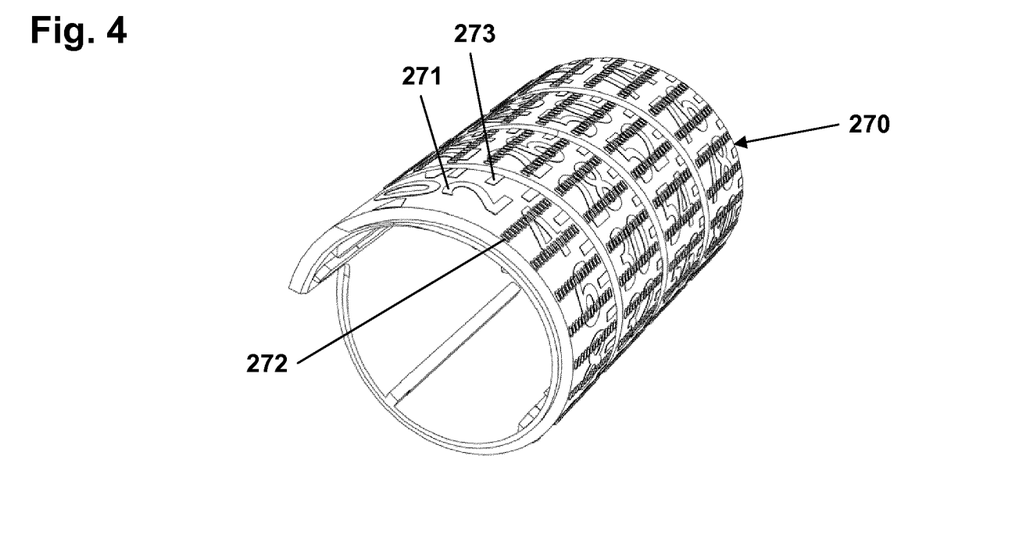
FIG. 4 shows a scale drum comprising code markings.

Turning to FIG. 4 a scale drum 270 with the same general design as the scale drum 170 described with reference to FIGS. 1-3 is shown, the scale drum comprising a helically arranged row of user-readable indicia 271 indicating dose sizes from 0 to 80 units of insulin in increments of one unit. For each incremental position of the scale drum a code pattern 272 is provided on the scale drum on a corresponding position. Depending on the positions of the dose window 202 (see FIG. 7) and the sensor assembly the code pattern may be off-set more or less from the user-readable indicia, e.g. two increments corresponding to an off-set of 30 degrees.

Each individual code pattern comprises a number of positions in which a marker, e.g. a dot or a line, may be provided. By omitting some of the markers a unique digital code can be provided for each position of the scale drum. For the shown embodiment in which the code pattern is arranged across the user-readable indicia, the markers may be provided by printing with a non-coloured transparent ink invisible or near-invisible to the human eye, however, for illustration purposes the markers are shown visible to the eye. Depending on the number of markers and the design of the coding each code pattern may contain the given position more than once providing redundancy. To provide the ink used for the printing process with sufficient electric conductivity to influence the electric field of a capacitor, the ink may contain added Ag (silver) or Graphene/carbon nanotubes to provide the ink with electrical conductivity.

Alternatively a non-transparent code pattern may be "hidden", i.e. not recognisable to the naked eye, in the user-readable indicia, e.g. the increment lines 273. In a further alternative some of the index numbers may be printed with conductive ink and designed to cooperate with a capacitive sensor assembly which is not arranged at a specific location but distributed circumferentially relative to the scale drum (see below).

To allow for cost-effective manufacturing both the visible and invisible indicia and code patterns may be provided on the scale drum in a combined printing process, e.g. having two ink cartridges in an ink jet printer that prints text, numbers or symbols on a component, selected parts of the print can be made with conductive ink, whereby a detectable marking can be printed at a very low cost on an object to be traced by a number of capacitive sensors strategically placed in the device.

Figure 5A:
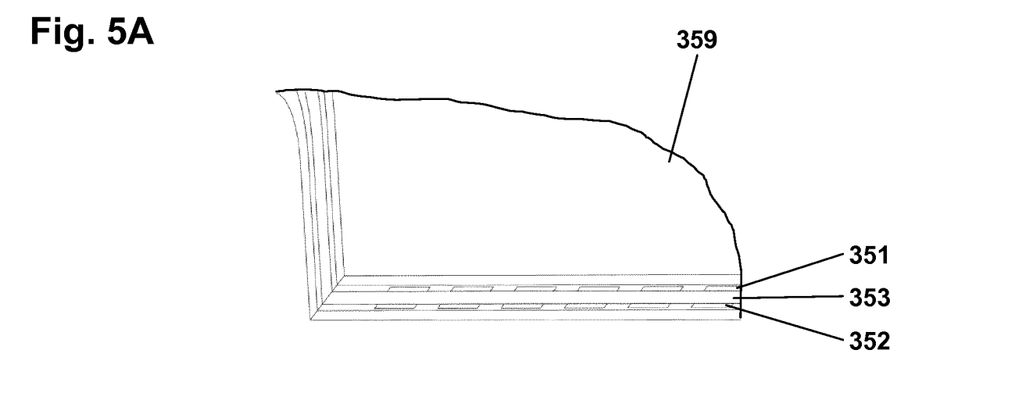
FIGS. 5A and 5B show a capacitive sensor assembly.
Figure 5B:
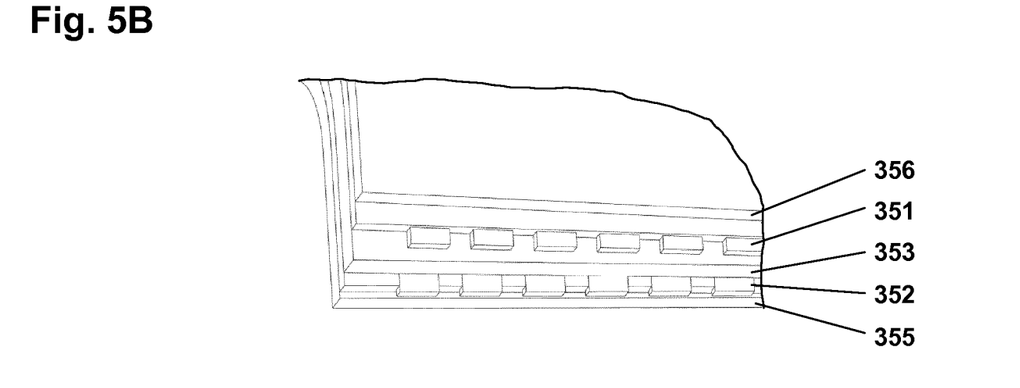

Turning to FIG. 5A a capacitive sensor assembly is shown. The sensor assembly is arranged at a free edge of flexible laminated member 359 and comprises a plurality of sensor pairs, each pair comprising two sensor plates (or pads) 351, 352 arranged at a distance from each other with an insulator 353 arranged there between. In FIG. 5B the different layers of the laminate has been exposed to better disclose the design, the laminate comprising a carrier foil 355, a layer with first sensor plates 352 and associated conductors arranged between an insulating filler, an insulator sheet 353, a layer with second sensor plates 351 and associated conductors arranged between an insulating filler, and a cover foil 356.

The above-described conductive code patterns and corresponding capacitive sensor arrangement and associated may be incorporated into a drug delivery device in a number of ways. With reference to schematic FIGS. 6A-6C examples in the form of a unitary concept, a two-unit concept and a two-unit concept adapted to cooperate with an external device in the form of e.g. a smartphone will be described.

Figure 6A:
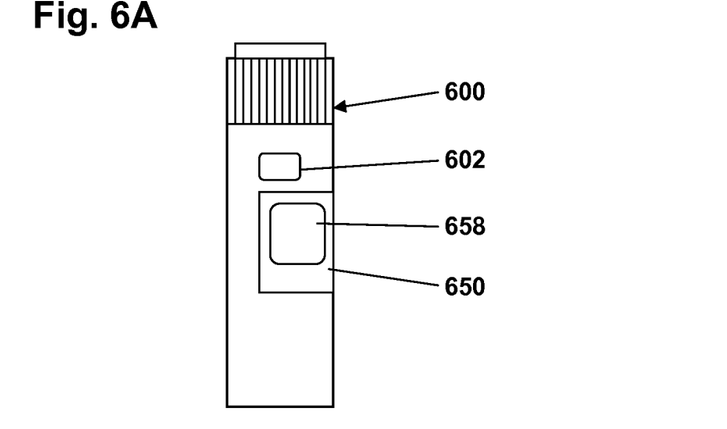
FIGS. 6A-6C show schematically different system concepts.

FIG. 6A discloses a self-contained drug delivery system of the pen-type (proximal portion only) adapted to determine and display dose-related information. The system comprises a drug delivery device 600 of the above-described type comprising a scale drum provided with conductive code markings as shown in FIG. 4, the currently set dose size being visible through an opening 602, as well as a sensor unit in the form of a flexible sheet-like "electronic label" 650. The electronic label is in the form of a flexible carrier sheet on which a number of structures are mounted or formed.

More specifically, the label is formed from a polymeric flexible sheet substrate and comprises a printed display 658 (see also FIG. 8), either a printed logic unit or a mounted chip (or a combination of the two), at least one battery which is either printed onto the substrate, laminated or mounted to it, input means in the form of a capacitive sensor assembly arranged at the edge of a tongue portion (see FIG. 6D), and a printed circuit comprising a plurality of individual leads connecting terminals of the different components, thereby forming the circuitry for energizing the sensor assembly. The electronic processor circuitry is configured to determine on the basis of a detected code a rotational position of the moveable indicator element, and calculate an expelled or set dose amount based on determined rotational positions of the moveable indicator element. A memory is provided for storing one or more dose events, e.g. characterized by dose size and a time stamp.

To ensure that the size of an expelled dose is reliably captured, the label electronics may be designed to determine a dose size only when the scale drum is rotated from a given set position to zero, this as described below with reference to FIGS. 7 and 8. To ensure low energy consumption the label electronics will be in a sleep state when not in use and would thus have to wake up prior to or during use. This may be accomplished automatically by additional switch circuitry adapted to detect movement of components in the drug delivery device, or more simply by a "button" on the label which would have to be actuated by the user prior to use. The display may be of the printed ink-type which mainly uses energy when changing state.

An antenna may also be formed on the flexible sheet by printing, the processor being adapted to transmit data to an external receiver via the antenna. The design and manufacture of an "electronic label" incorporating e.g. printed electronics is described in greater detail in WO 2015/071354 which is hereby incorporated by reference.

To reduce costs when the label is applied to a disposable device one or more of the above-described non-sensor assembly components may be arranged in a separate auxiliary device which then is to be used for a longer period.

Figure 6B:
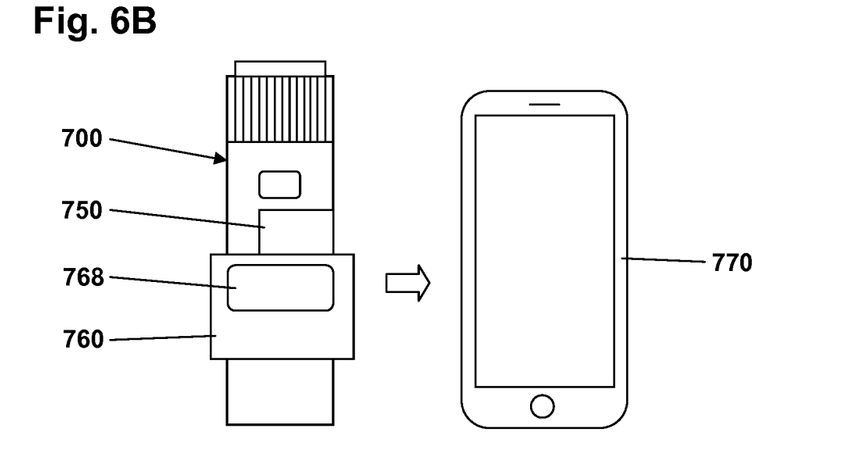

Correspondingly, FIG. 6B shows a two-unit drug delivery system in which the majority of the above-described label components have been arranged in an auxiliary add-on unit adapted to be mounted on the drug delivery in a mating relationship with the label, e.g. by means of a pair of flexible gripping arms allowing the add-on unit to be clipped onto and subsequently removed from the drug delivery device.

More specifically, the label 750 merely comprises the capacitive sensor assembly arranged at the edge of a tongue portion as well as the circuitry for energizing the sensor assembly in the form of an array of galvanic contacts adapted to engage corresponding contacts on the add-on unit 760. Correspondingly, the add-on unit further comprises electronic processor circuitry configured to determine rotational positions of the moveable indicator element on the basis of detected codes and calculate an expelled or set dose amount based on determined rotational positions of the moveable indicator element, an energy source for energizing the sensor assembly and the electronic processor circuitry, and a memory adapted to store dose related data, the memory being controlled by the electronic processor circuitry. To make the calculated dose amounts available to a user the add-on unit may be provided with a display 758 and/or transmission means for wirelessly transfer dose data to an external device such as a smartphone.

In a simple version of such an add-on unit the unit merely serves to collect and store locked data and subsequently transmit the data to an external unit such as a smartphone 770. Communication between the add-on unit and the external device may be initiated and controlled by the latter, e.g. using means of communication such as NFC being powered from the smartphone, this reducing the energy requirements for the add-on unit thus serving to further lower the costs.

Figure 6C:
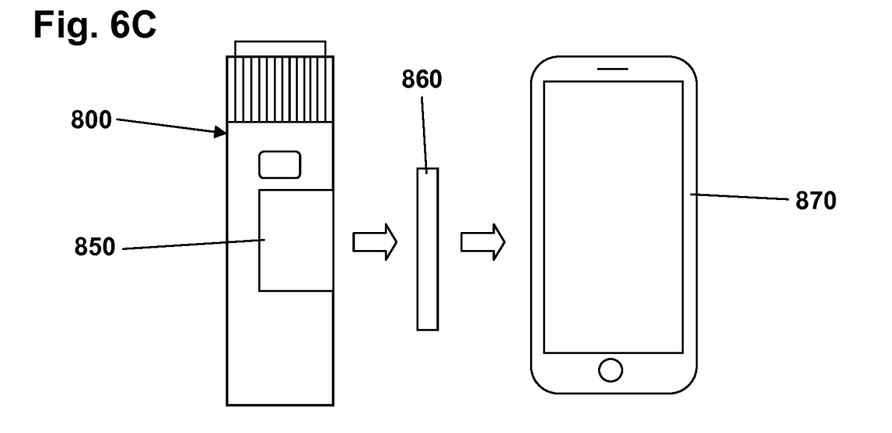

With reference to FIG. 6C a further system is shown in which the add-on unit is adapted to serve as a wireless transmitter link unit 860 between the electronic label 850 of the drug delivery device 800 and the external device 870, e.g. a smartphone. The electronic label comprises the circuitry necessary to detect and store a number of log entries as well as first wireless transmission means. To provide a system which has a high degree of user-friendliness the transmitter unit should ensure that captured data from the drug delivery device is transmitted to the external device with as few requirements as possible to the user. Indeed, it could be argued that it would be even more convenient if no transmitter unit was required, however, it is not deemed cost-effective to provide a relatively inexpensive disposable drug delivery device with the means and the power to allow communication via the wireless communication typically incorporated in a smartphone such as Bluetooth®. Also NFC would be an option, however, currently NFC is not incorporated or made available in the majority of smartphones on the market.

Correspondingly, the transmitter unit comprises first "close range low power" wireless transmission means for communication with the electronic label as well as "longer range high power" wireless transmission means for communication with the external device.

An example of "close range low power" wireless transmission means could be passive NFC, i.e. transmission powered by the transmission unit, this providing no power consumption in the electronic label, however, in most cases the two communicating units have to be arranged in close proximity to each other and with a specific orientation there between. Ideally, the two units should establish transmission of data when they are merely "in proximity" to each other, e.g. when the drug delivery device is placed on a night table next to the transmission unit or when both units are stored in the same e.g. pocket or case. An example of a technology providing this functionality would be RFID-based communication, i.e. using one of the different RFID protocols for transmission of dynamic data (in contrast to the transmission of non-dynamic ID data mostly associated with RFID data transfer). The RFID technology may be an Active Reader Passive Tag (ARPT) system has an active reader, which transmits interrogator signals and also receives authentication replies from passive tags, or an Active Reader Active Tag (ARAT) system uses active tags awoken with an interrogator signal from the active reader. A variation of this system could also use a Battery-Assisted Passive (BAP) tag which acts like a passive tag but has a small battery to power the tag's return reporting signal. Depending especially of the wave length used the communication range may in the cm or meter range.

The "longer range high power" wireless transmission means could be in the form of Bluetooth® which currently is the most common wireless means in use or Bluetooth® low energy (BLE). As the transmission unit may be placed stationary, e.g. on a night table, or carried in a bag or purse, the requirements as to size and weight would allow power to be supplied by a replaceable battery.

Figure 6D:
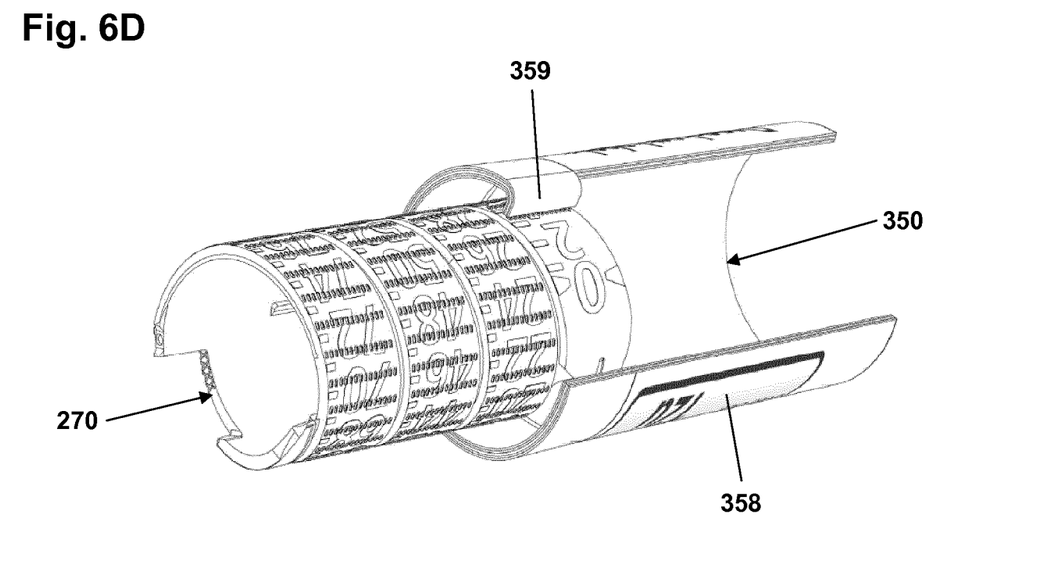
FIG. 6D shows components of a capacitive sensor system comprising an electronic label.

FIG. 6D shows the two main components of a capacitive sensor system comprising the indicator element in the form of a scale drum 270 provided with conductive code markings as shown in FIG. 4, as well as a sensor unit in the form of a flexible sheet-like "electronic label" 350. The electronic label is in the form of a flexible carrier sheet on which a number of structures are mounted or formed. The shown exemplary embodiment represents the system concept of FIG. 6A and the specific sensor arrangement are adapted to be used with a pen device of the type disclosed in FIGS. 5-3 and described above.

More specifically, the label is formed from a polymeric flexible sheet substrate and comprises a printed display 358 (see also FIG. 8), either a printed logic unit or a mounted chip (or a combination of the two), at least one battery which is either printed onto the substrate, laminated or mounted to it, input means in the form of a capacitive sensor assembly arranged at the edge of a tongue portion 359, and a printed circuit comprising a plurality of individual leads connecting terminals of the different components. An antenna may also be formed on the flexible sheet by printing, the processor being adapted to transmit data to an external receiver via the antenna.

Besides the obvious advantages of very low costs of implementing positional markings by printing the markings with conductive ink, the reading of the markings with an array of capacitive sensors (as used in capacitive fingerprint scanners) improves freedom of design by not requiring specific shapes or mechanical properties. Nor does this solution require physical contact between the marked component and the sensor or wiring inside the device or any other physical connection between the component to be monitored and the electronic circuitry with integrated sensors.

Since capacitive sensors are basically very simple, they may be printed as part of a printed electronic circuit, thereby solving connection issues between sensors and printed electronic circuitry. This would allow low production cost and low use of resources and materials to dispose of and thereby make implementation of such systems in disposable devices economical and environmentally feasible.

Different capacitive sensing principle may be implemented. A first principle is the one commonly used in commercially available fingerprint scanners, e.g. as on laptops, where the user slides a finger across a line of sensors. The electric field is influenced by the ridges and valleys of the fingerprint and since the influence varies with distance, the variation in distance between the sensor elements and the ridges and valleys of the fingerprint, gives variation in signal response from the sensor elements. This principle is based on registration on variations in signal strength from each of the sensor elements in the line of sensors to provide a unique code for a given pattern of valleys and ridges. A second principle is not based on signal strength, but on phase of the received signal. In this principle, a varying signal of either different frequency or different phase is applied to two transmitters. A signal is then induced in a common receiver, if an electrical conductor is placed close to one or both of the transmitters and the receiver. The phase and frequency of the signal induced in the receiver will depend on the distance between the coupling object and the one transmitter and the receiver relative to the distance between the coupling object and the other transmitter and the receiver. For both principles, the sensor elements basically consist of two (small) plates of an electrical conductor placed close to each other with a layer of insulation between them.

Figure 7:
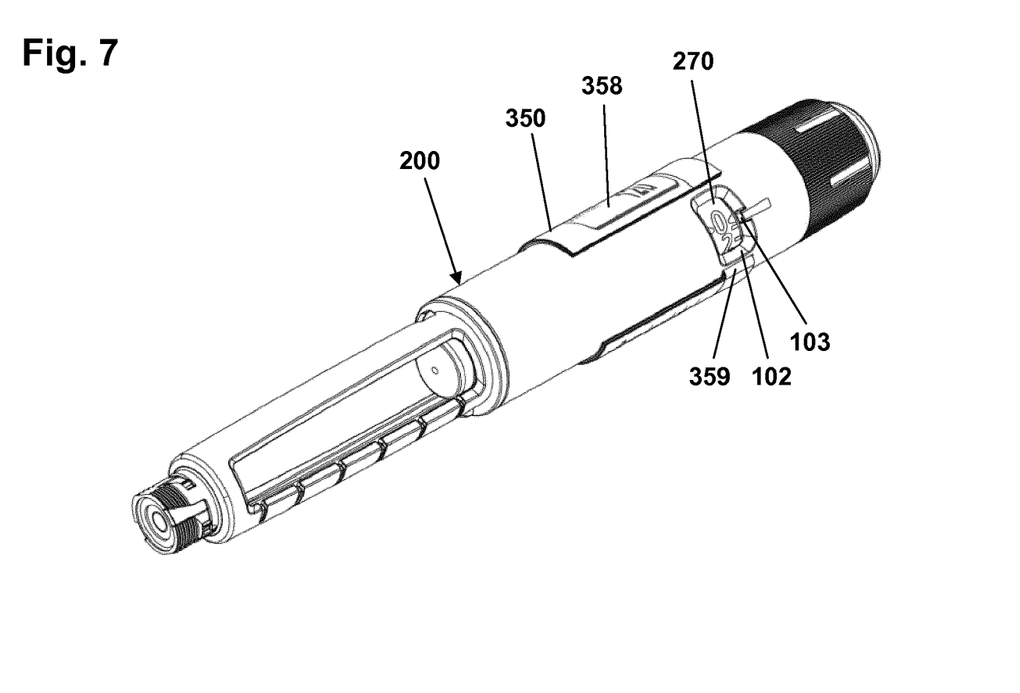
FIG. 7 shows a drug delivery device comprising the sensor system of FIG. 6D.

In FIG. 7 the label is shown mounted on a corresponding drug delivery device 200, e.g. by adhesive. In addition to the scale drum 270 which has been provided with conductive code markings, the device housing has been provided with a slit formed opening in the vicinity of the display window, this allowing the flexible tongue portion 359 of the label to be mounted through the slit opening with the edge of the capacitive sensor assembly arranged in close proximity to the scale drum outer surface and in parallel therewith, see FIG. 6D. With the individual code patterns off-set 30 degrees relative to the portion of the scale drum arranged in alignment with the window pointer 203, the sensor assembly and label electronics will be able to determine the dose size as displayed to the user in the window 202.

Figure 8:
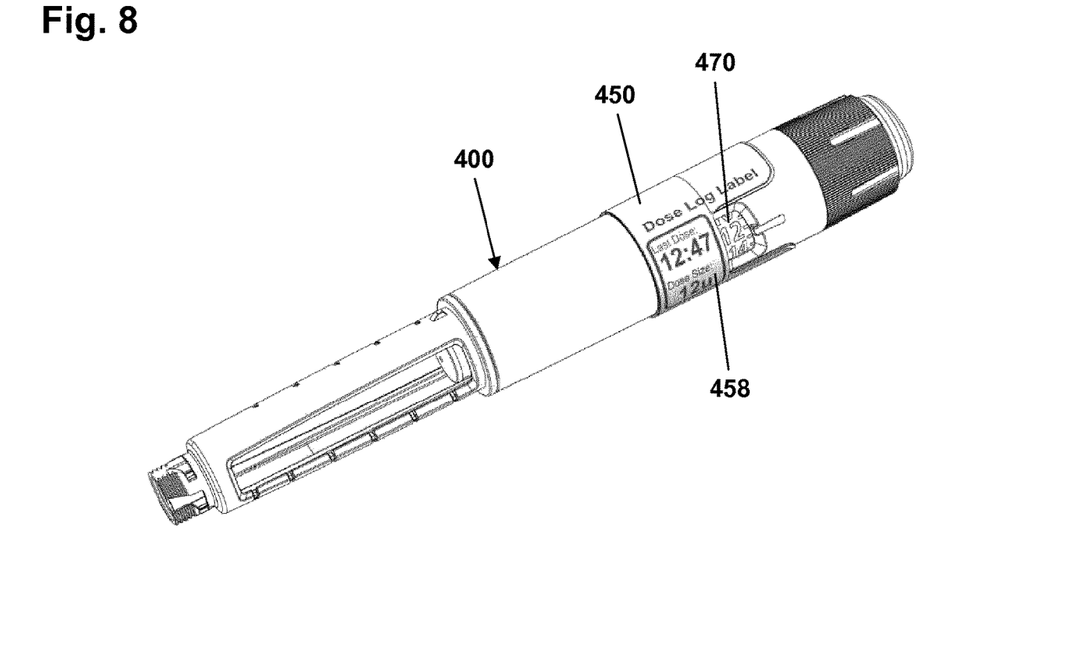
FIG. 8 shows a drug delivery device comprising an alternative capacitive sensor system.

In the shown embodiment the label is designed to display the time since the last dose was expelled as well as the size of the dose, see FIG. 8. As determination of an expelled dose is based on detection of the rotational start and the end position of the scale drum at the beginning and the end of a dosing event, it is important to ensure that the real start and end position are detected and not scale drum positions during dose setting.

In the shown embodiment the sensor set-up is relatively simple comprising only the described rotational position sensor. To ensure that the size of an expelled dose is reliably captured, the label electronics may be designed to determine a dose size only when the scale drum is rotated from a given set position to zero. To properly capture the start position a number of conditions may have to be met. For example, a start position is determined when (i) the scale drum has not been adjusted within a given amount of time, e.g. 5 seconds, and (ii) the spring-driven scale drum rotates to the zero position with a given rotational speed and profile, the latter being determined as the code patterns pass the sensor. In case the conditions are not met no dose size will be determined and an error message may be displayed. Indeed, such a set-up may be considered relatively simple as it would not allow e.g. a dosing event to be paused.

Correspondingly, in an alternative embodiment (not shown) the electronic label may be provided with a further sensor adapted to sense whether the drug delivery device is in a dose setting or dose expelling mode. The mode sensor may be a capacitive sensor of the same general design as described above, and be adapted to detect a translational movement of a member indicate of the state of the delivery device. An example of such a member is the ring-formed clutch element 140 which is moved between first and second axial positions when the release button 190 is moved axially back and forth between the dose setting and the dose release position. The code marking on the clutch element may be in the form of a circumferential printed code pattern. The corresponding sensor assembly may be formed on a further label tongue portion adapted to be arranged through an opening in the device housing.

Figure 9:
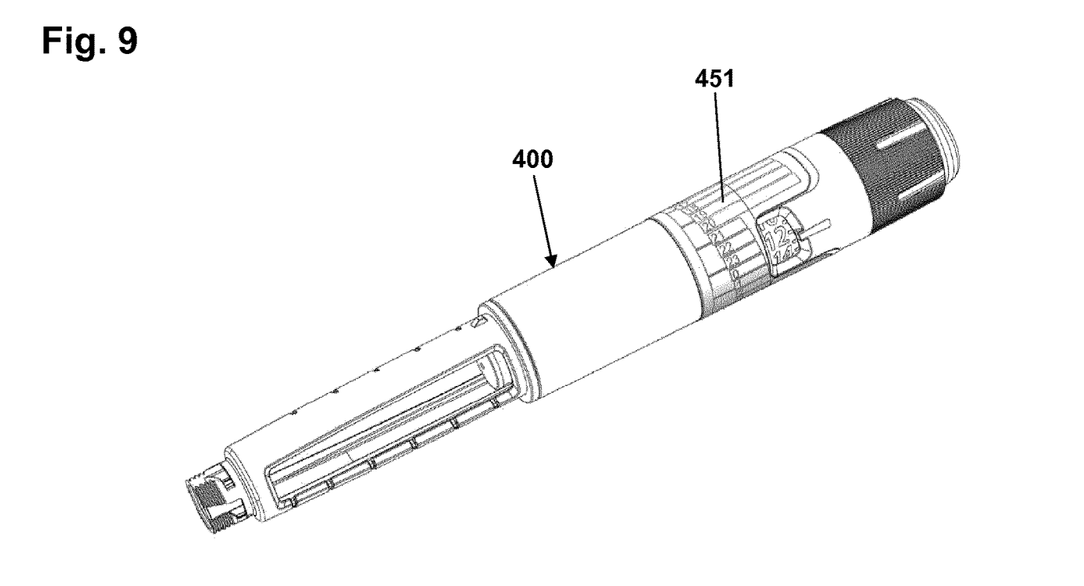
FIG. 9 shows the drug delivery device of FIG. 8 with layers of the label removed to show the capacitive sensor plates.

With reference to FIGS. 8 and 9 a further embodiment of a coded scale drum and an electronic label 450 with a capacitive sensor arrangement adapted to be mounted on an exterior surface of a drug delivery device 400 will be described. In contrast to the above-described embodiment in which the scale drum was provided with discrete code patterns for each incremental rotational position, the scale drum 470 is provided only with the traditional indicia visible to the user. However, a number of the indicia 471 are printed with conductive ink allowing the indicia to be detected by a plurality of capacitive sensor plates formed circumferentially on the inner surface of the label, the number of plates and the position of the conductive dose numerals on the scale drum being designed to indicate the position of the scale drum relative to the housing. As appears, in such a system, the unique code corresponding to a given position is not given in the marking itself, but by the position of the marking relative to the sensors and thus the combination of sensors that detects one or more marking. As shown in FIG. 9 the individual capacitive sensor plates 451 are larger than those of the first embodiment, this compensating for the larger distance as well as the housing material arranged between the sensor plates and the outer surface of the scale drum. As appears, the label has no sensor assembly tongue portion arranged through a slotted opening in the housing, this allowing for simpler mounting on an unmodified housing 400. Otherwise the label 450 appears identical to the user with a display 458. Correspondingly, similar large sensor plates may also be used to detect the axial position of the clutch element 140 and thereby the setting or dosing state of the device.

Figure 10A:
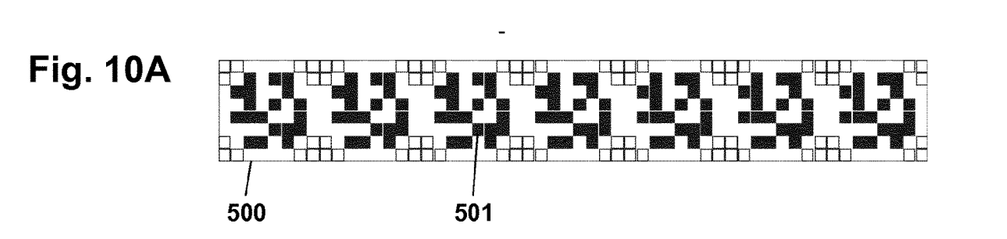
FIGS. 10A-10C show a label with printed information.
Figure 10B:
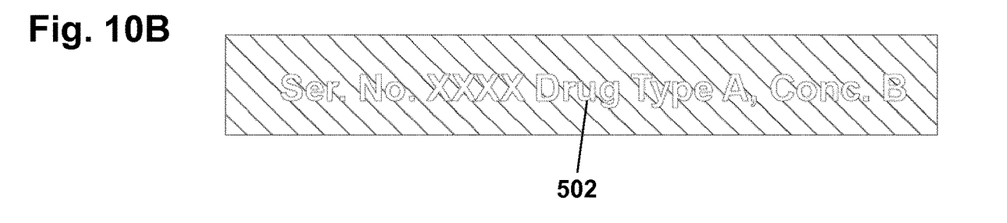
Figure 10C:
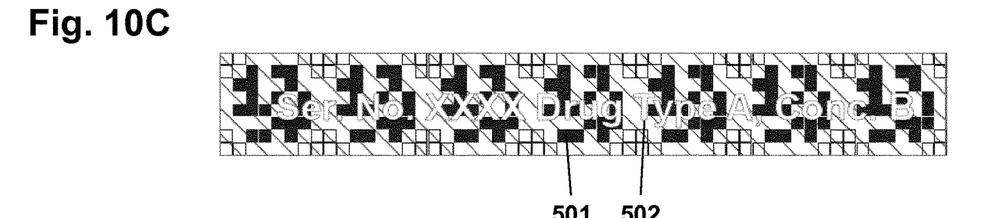
Figure 11:
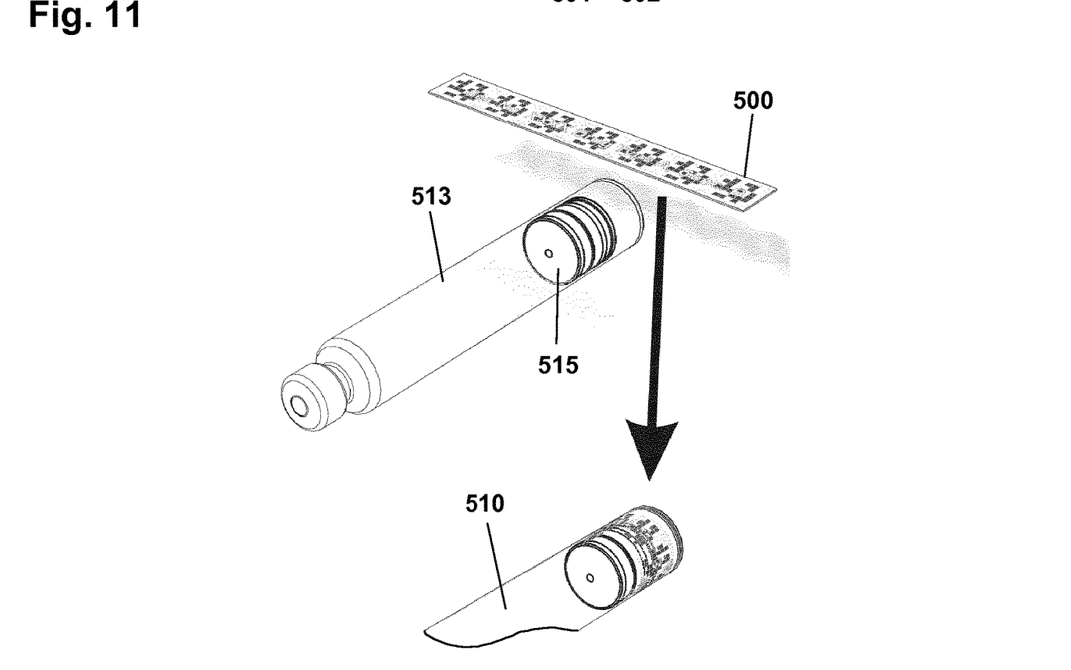
FIG. 11 shows a drug cartridge with the label of FIG. 10C applied.

Based on the concept of printing visible and non-visible information on a surface, a coded cartridge will be described. More specifically, FIG. 10A shows a code pattern 501 printed with a conductive ink on a strip-formed label 500, FIG. 10B shows user-readable drug information 502 printed on the same kind of label, and FIG. 10C shows the same two prints 501, 502 printed on top of each other on the same label. The code pattern is printed with ink invisible or near-invisible to the human eye. As shown in FIG. 11 the label 500 is adapted to be attached circumferentially on the proximal portion of a drug cartridge 513 comprising an axially displaceable piston 515. The code pattern comprises a plurality of identical code areas each coding for the same information, e.g. type of drug, concentration of drug and a serial number for the cartridge. Having the same code area printed a number of times on the circumference of the cartridge allows the information to be read by a relatively small capacitive sensor area without the need for the cartridge to be rotationally positioned relative to the sensor. The capacitive sensor may be provided utilizing printing methods as described above and may be incorporated in the cartridge holder of a drug delivery device.

By utilizing a non-visible code printed overlapping with a visible code a number of advantages can be achieved. For example, both types of information can be printed during the same process, the label can be made smaller which is of advantage due to the small size of the drug cartridge, the user is not faced with non-understandable information, the visual appearance is the same as for a non-coded cartridge which may be relevant when complying with regulative requirements, just as the invisible coding may provide an effective means for preventing counterfeiting.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery device comprising or adapted to receive a cartridge with an axially displaceable piston, the drug delivery device comprising:
   a housing having an exterior,
   a stationary capacitive sensor assembly,
   a moveable indicator element comprising a surface with a code pattern detectable by the stationary capacitive sensor, the code pattern being formed from conductive markings printed onto the surface, and
   a flexible sheet on which is formed or mounted:
      the stationary capacitive sensor assembly,
      circuitry for energizing the sensor assembly, and
      a communication structure adapted to communicate data related to detected code information,
   wherein the flexible sheet is mounted at least in part to the exterior of the housing.

2. The drug delivery device as in claim 1, further comprising electronic processor circuitry formed on or mounted to the flexible sheet and associated with the stationary capacitive sensor assembly, the electronic processor circuitry being configured to:
   (i) determine on the basis of detected code a rotational position of the moveable indicator element, and
   (ii) calculate an expelled or set dose amount based on determined rotational positions of the moveable indicator element.

3. The drug delivery device as in claim 2, further comprising a display formed on or mounted to the flexible sheet and adapted to display dose related data, the display being controlled by the electronic processor circuitry.

4. The drug delivery device as in claim 2, further comprising a memory formed on or mounted to the flexible sheet and adapted to store dose related data, the memory being controlled by the electronic processor circuitry.

5. The drug delivery device as in claim 1, further comprising communication structure formed on or mounted to the flexible sheet and adapted to transmit or transfer dose related data to an auxiliary or external device.

6. The drug delivery device as in claim 1, further comprising an energy source.

7. The drug delivery device as in claim 1, in combination with an auxiliary device, the auxiliary device comprising:
   first communication structure adapted to receive dose related data detected by the capacitive sensor assembly.

8. The drug delivery device as in claim 1, in combination with an auxiliary device adapted to be associated with the drug delivery device, the auxiliary device comprising:
   a first communication structure adapted to receive dose related data detected by the capacitive sensor assembly,
   wherein the combination comprises the further components:
   electronic processor circuitry configured to:
      (i) determine on the basis of detected code a rotational position of the moveable indicator element, and
      (ii) calculate an expelled or set dose amount based on determined rotational positions of the moveable indicator element,
   an energy source for energizing the sensor assembly and the electronic processor circuitry, and
   a memory adapted to store dose related data, the memory being controlled by the electronic processor circuitry.

9. The combination as in claim 8, wherein the drug delivery device comprises:
   the electronic processor circuitry,
   the memory adapted to store dose related data,
   a display adapted to display dose related data and controlled by the electronic processor circuitry, and
   the energy source for energizing the sensor assembly and the electronic processor circuitry.

10. The combination as in claim 9, wherein the first communication structure is adapted to receive dose data by wireless transmission, or
   the auxiliary device is adapted to be releasably attached to the drug delivery device, the first communication structure being adapted to receive dose data by galvanic or wireless transmission.

11. The combination as in claim 8, the auxiliary device further comprising:
   a second communication structure adapted to transfer or transmit received dose related data to an external device.

12. The drug delivery device as in claim 1, wherein:
   the moveable indicator element is adapted to rotate relative to the stationary capacitive sensor assembly and corresponding to a general axis, the code pattern being indicative of the rotational position of the moveable indicator element relative to the stationary capacitive sensor assembly.

13. The drug delivery device as in claim 12, wherein:
   the moveable indicator element is adapted to rotate helically relative to the stationary capacitive sensor assembly, the code pattern being arranged helically on the surface and being indicative of the rotational and/or axial position of the moveable indicator element relative to the stationary capacitive sensor assembly.

14. The drug delivery device as in claim 12, comprising:
   a dose setting and dose expelling mechanism comprising a scale member provided with a plurality of user-readable dose size indices, the scale member forming the moveable indicator element, the scale member being rotated from an initial position to a set position when a dose is set and rotated from the set position to the initial position when the set dose is expelled,
   wherein the housing comprises an opening arranged to show a scale member dose size indicia corresponding to a set dose.

15. The drug delivery device as in claim 14, wherein the code pattern is printed on surface portions of the scale member which passes the housing opening as the scale member rotates during dose setting, and
   wherein the code pattern is printed with material being non-visible to the human eye, or a portion of the user-readable dose size indices are printed with conductive material to provide the code pattern.

* * * * *

UNITED STATES PATENT AND TRADEMARK OFFICE
CERTIFICATE OF CORRECTION

PATENT NO. : 10,850,041 B2
APPLICATION NO. : 15/772619
DATED : December 1, 2020
INVENTOR(S) : Larsen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 225 days.

Signed and Sealed this
Thirty-first Day of January, 2023

Katherine Kelly Vidal
*Director of the United States Patent and Trademark Office*